United States Patent [19]

Telschow

[11] Patent Number: 5,068,426

[45] Date of Patent: Nov. 26, 1991

[54] PURIFICATION OF N,N-DIALKYLCARBAMOYLMETHYLPHOSPHINE OXIDE

[75] Inventor: Jeffrey E. Telschow, Tarrytown, N.Y.

[73] Assignee: Akzo NV, Arnhem, Netherlands

[21] Appl. No.: 467,712

[22] Filed: Jan. 19, 1990

Related U.S. Application Data

[63] Continuation-in-part of Ser. No. 370,227, Jun. 22, 1989, abandoned.

[51] Int. Cl.$^5$ .............................................. C07F 9/28
[52] U.S. Cl. ...................................... 564/15; 556/15; 556/16
[58] Field of Search ....................... 564/15; 556/15, 16

[56] References Cited

U.S. PATENT DOCUMENTS 4,548,790 10/1985 Horwitz et al. ..................... 564/15

Primary Examiner—Donald G. Daus
Assistant Examiner—Jyothsna Denkat
Attorney, Agent, or Firm—Richard P. Fennelly; Louis A. Morris

[57] ABSTRACT

Crude organic solutions of N,N-dialkylcarbamoylmethylphosphine oxide compounds can be purified by treatment with a first row transition metal salt to form a complex which can be treated to regenerate a purified solution of the compound. The first row transition metal can be selected from the monobasic acid salts of zinc, for example.

16 Claims, No Drawings

PURIFICATION OF N,N-DIALKYLCARBAMOYLMETHYLPHOSPHINE OXIDE

This application is a continuation-in-part of U.S. Ser. No. 370,227, filed June 22, 1989, now abandoned.

BACKGROUND OF THE INVENTION

1. Field of the Invention

The instant invention relates to a process for purifying N,N-dialkylcarbamoylmethylphosphine oxide compounds (hereinafter referred to as "CMPO's").

2. Description of the Prior Art

CMPO's are useful as transuranium extractants. It is known to purify crude CMPO compounds dissolved in an organic solvent, for example, from about 65% assay to much higher assay (e.g., about 98%) by precipitating them using mercuric nitrate followed by regeneration of the CMPO using potassium cyanide and sodium carbonate as described on page 404 of Separation Science and Technology, 16(4), 403–416 (1981). Both the mercury and cyanide moieties used in such a procedure are undesirably toxic. In addition, mercury compounds are expensive.

SUMMARY OF THE INVENTION

The instant invention relates to the purification of crude CMPO compounds dissolved in an organic solvent by treating them with a first row transition metal salt to form a complex therefrom which can be used to regenerate a purified organic solution of the CMPO.

DETAILED DESCRIPTION OF THE INVENTION

The instant process involves the purification of a crude CMPO composition comprising an organic solvent, CMPO compound, and impurities associated with the synthesis of the CMPO (e.g.), including N,N-dialkylcarbamoylmethyl halides, secondary and tertiary phosphine oxides, phosphinic acids, and the like. The purification procedure involves the essential step of adding a first row transition metal salt to such a composition to form a complex with the CMPO. The first row transition metals usable herein include manganese, cobalt, nickel, copper and zinc. They are of less expense than other transition metals and do not possess the toxicity of mercuric nitrate. The first row transition metals also tend to form complexes faster and more completely than mercury compounds. Horwitz et al. (in Solvent Extraction and Ion Exchange, 4, 449, 1986) describes a study of the extraction (complexation) ability of various CMPOs for aqueous nitric acid solutions of metals. He mentions that the smaller first row transition metals are not extracted to any significant extent by CMPOs compared with the larger actinide and lanthanide and with selected second and third row transition metals. Thus, it is not deemed to be obvious to consider the use of first row transition metals in forming purifiable complexes with CMPOs.

The complex that is formed in accordance with the present invention can be used to regenerate a more pure CMPO composition. In accordance with one embodiment of the invention, the complex that is formed is a water- and solvent-insoluble solid precipitate. Such a precipitate can be isolated, washed, if necessary, and redissolved in a composition of an aqueous base (e.g., NaOH, aqueous NH$_3$, and the like) and organic solvent to regenerate a more pure organic solvent/CMPO composition. For example, in the case of the use of zinc chloride, the use of excess base causes zinc hydroxide formed in the following reaction (1) to form a water-soluble salt as shown in (2).

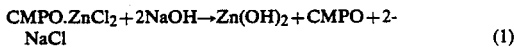

$$CMPO \cdot ZnCl_2 + 2NaOH \rightarrow Zn(OH)_2 + CMPO + 2NaCl \quad (1)$$

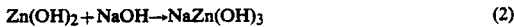

$$Zn(OH)_2 + NaOH \rightarrow NaZn(OH)_3 \quad (2)$$

In a second embodiment of the instant invention, the complex that is formed is a liquid or is heated above its melting point (e.g., 70°–80° C. in the case of some of the zinc complexes described herein). The liquid or molten salt can then be extracted with a suitable solvent (e.g., heptane) to remove undesired impurities. This embodiment obviates the need to filter a precipitate, and wash, dry and transfer the resulting solid. It saves both processing steps and time.

The salts described herein that have been found to be effective in the practice of the invention include such inorganic salts of strong (monobasic) acids of the first row transition metals such as the chlorides, the nitrates, the bromides and the tetrafluoroborates thereof. The amount of salt which can be added can range from about 5% to about 100%, by weight of CMPO. The concentration of CMPO in the organic solvent can range from about 5% to about 50%, by weight of the solvent.

The following Examples illustrate the invention and the effects of the metal's counterion and solution medium on complex formation and physical form.

EXAMPLES 1–26

Dilute (e.g., 10–25%) solutions of N,N-bis(2-methylpropyl)-2-(octylphenylphosphinyl)acetamide in hexane were combined with a variety of aqueous metal solutions and stirred rapidly to observe any precipitate formation (the desired result) or color change. The runs were performed in small test tubes which were stirred on a VORTEX-GENIE mixer for about one-half minute at room temperature. The following results were obtained:

| Example No. | Compound(s) Added | Observations |
| --- | --- | --- |
| 1 | MgSO$_4$ | No change (NC) |
| 2 | CaCl$_2$ | NC |
| 3 | BaO + HNO$_3$ | Brownish color in hexane layer |
| 4 | MnCl$_2$ | NC |
| 5 | MnCl$_2$ + HNO$_3$ | Some oily light colored precipitate |
| 6 | FeCl$_3$ | Yellow-brown semi-solid forms |
| 7 | Fe$_2$(SO$_4$)$_3$ | NC |
| 8 | Fe$_2$(SO$_4$)$_3$ + HNO$_3$ | Yellow-brown color in hexane layer |
| 9 | CoCl$_2$ | Blue solid forms very slowly |
| 10 | CoBr$_2$ | Pink solid forms rapidly |
| 11 | Co(OAc)$_2$ | NC |
| 12 | Co(OAc)$_2$ + NH$_3$ | NC |
| 13 | Co(OAc)$_2$ + HNO$_3$ | Some yellowish color in hexane layer |
| 14 | NiCl$_2$·DME | NC |
| 15 | NiCl$_2$ + NH$_3$ | NC |
| 16 | Ni(BF$_4$)$_2$ | Rapid light green oily precipitate |
| 17 | CuCl$_2$ | Yellow solid forms |
| 18 | Cu(NO$_3$)$_2$ | NC |
| 19 | Cu(NO$_3$)$_2$ + NH$_3$ | NC |
| 20 | Cu(NO$_3$)$_2$ + HNO$_3$ | NC |
| 21 | Zn(OAc)$_2$ | NC |

-continued

| Example No. | Compound(s) Added | Observations |
|---|---|---|
| 22 | Zn(OAc)$_2$ + HNO$_3$ | NC |
| 23 | ZnCl$_2$ | Slow formation of white solid |
| 24 | Zn(NO$_3$) | Rapid formation of white solid |
| 25 | Zn(BF$_4$)$_2$ | Rapid formation of white solid |
| 26 | HgO + HNO$_3$ | Slow formation of white oily solid |

Note: OAc = acetate; DME = 1,2-dimethoxyethane

EXAMPLES 27–36

A solution (or partial suspension) of 1.0 mmole of metal salt in 0.35 ml of methanol was shaken well with a solution of 1.0 mmole of 93% CMPO in 2.0 ml of hexane. The selectivity of the salt for complexation with CMPO and its main impurity, dioctylphenylphosphine oxide (DOPPO), was compared by gas chromatographic analysis of the hexane solution after reaction. The relative amounts of DOPPO and CMPO remaining are expressed below as a ratio. Selectivity for removal of CMPO rather than DOPPO increases as this ratio increases. With zinc chloride (Example 27), concentration of DOPPO and CMPO left in the hexane are defined as 1.00 in each case. Concentrations in other Examples are given relative to this one. Thus, the larger the value for the DOPPO concentration, the better this impurity was removed from CMPO. And, the smaller the CMPO concentration, the more completely it was removed from hexane solution.

| Example No. | Compound Added | Complex Observed | Relative DOPPO | Conc. CMPO | Ratio of DOPPO/CMPO |
|---|---|---|---|---|---|
| 27 | ZnCl$_2$ | white solid | 1.00 | 1.00 | 0.39 |
| 28 | Zn(NO$_3$)$_2$ | colorless liquid | 0.97 | 0.54 | 0.70 |
| 29 | NiCl$_2$ | green liquid | 3.29 | 0.96 | 1.33 |
| 30 | Ni(NO$_3$)$_2$ | green liquid | 3.09 | 0.88 | 1.38 |
| 31 | MnCl$_2$ | white solid | 4.83 | 0.92 | 2.04 |
| 32 | CoCl$_2$ | blue solid | 5.57 | 0.74 | 2.96 |
| 33 | FeCl$_3$ | brown liquid | 0.93 | 1.59 | 0.23 |
| 34 | CuCl$_2$ | yellow liquid | 2.40 | 4.49 | 0.21 |
| 35 | HgCl$_2$ | colorless liquid* | 0.96 | 9.41 | 0.04 |
| 36 | Hg(NO$_3$)$_2$ | colorless liquid* | 2.71 | 5.85 | 0.18 |

*Partially solidified on long standing.

EXAMPLE 37

A 1 gram sample of crude CMPO (about 59.6 area % N,N-bis(2-methylpropyl)-2-(octylphenylphosphinyl)-acetamide by gas chromatography) was dissolved in about 5 ml of hexane and stirred with 2 ml of water containing 0.5 gram zinc chloride for forty-five minutes. The two phase mixture which resulted became a thick paste of white solids.

The mixture described above was allowed to stand over the weekend and was then diluted with hexane and water and filtered through a medium frit funnel. The white sludgy solid was washed with water and hexane. On air drying, the product became a slightly sticky amorphous solid which was stirred for about five minutes with 5 ml of hexane and 1 ml of 15% sodium hydroxide. The solids dissolved and the hexane layer was washed twice with additional water and stripped. The product (0.53 gram) showed about 93 area % CMPO by gas chromatography. The nmr was consistent with the structure for CMPO. The mother liquor portions and hexane washes of the zinc salt were stripped to 0.33 gram of a colorless oil which was about 20% CMPO by gas chromatographic analysis.

EXAMPLE 38

In a 3-neck 250 ml flask was placed 19.0 gm (40 mmoles) of CoCl$_2$ and 10 ml of methanol. The mixture was heated until almost all solids had dissolved to form a deep blue solution. A solution of 5.2 gm of 86.2% CMPO (40 mmoles) in 130 ml of hexane was added, and the mixture was stirred rapidly. The thick blue suspension was heated to 50° C. for 10 minutes, cooled to 30° C. and filtered. The blue solid was washed with 50 ml and then 20 ml of hexane, sucked fairly dry, and return to the reaction flask along with 100 ml of hexane.

This mixture was treated with 15 ml (170 mmoles) of 29% NH$_3$, added a little at a time to the stirred slurry. The lower red aqueous solution containing red solids was separated, and the organic phase was washed with a little NH$_3$ and then some chelating agent (DEQUEST 2000 brand) to remove traces of cobalt. After a wash with aqueous Na$_2$CO$_3$, the hexane was evaporated to leave 14.8 gm of purified CMPO with a purity of 97.8 area % by gas chromatographic analysis.

EXAMPLE 39

To a solution of 5.8 gm (12.2 mmoles) of 86.2% CMPO in 30 ml of hexane was added a hot suspension of 1.58 gm of NiCl$_2$ in 5 ml of methanol. The mixture was stirred very rapidly for 10 minutes and then allowed to settle. The clear hexane supernatant was decanted from the thick green liquid complex, which was agitated with another 30 ml of hexane for 10 minutes. After removing the solvent phase, the oil was treated with 30 ml of hexane and 4.3 ml (73.2 mmoles) of 29% NH$_3$. Work-up as in Example 38 gave 5.08 gm of 92.2 area % pure CMPO.

I claim:

1. A process for the purification of an N,N-dialkylcarbamoylmethylphosphine oxide compound (CMPO) dissolved in organic solvent which comprises treatment with a first row transition metal salt to form an insoluble complex therefrom which is then reacted with aqueous base to regenerate purified CMPO.

2. A process as claimed in claim 1 wherein the transition metal salt is a salt of a monobasic acid.

3. A process as claimed in claim 2 wherein the transition metal salt is a chloride.

4. A process as claimed in claim 2 wherein the transition metal salt is a nitrate.

5. A process as claimed in claim 2 wherein the transition metal salt is a tetrafluoroborate.

6. A process as claimed in claim 1 wherein the transition metal salt which is used ranges from about 5% to about 100%, by weight of the CMPO.

7. A process as claimed in claim 2 wherein the transition metal salt which is used ranges from about 5% to about 100%, by weight of the CMPO.

8. A process as claimed in claim 1 wherein the concentration of CMPO in the organic solvent ranges from about 5% to about 50%, by weight of the solvent.

9. A process as claimed in claim 2 wherein the concentration of CMPO in the organic solvent ranges from about 5% to about 50%, by weight of the solvent.

10. A process as claimed in claim 7 wherein the concentration of CMPO in the organic solvent ranges from about 5% to about 50%, by weight of the solvent.

11. A process as claimed in claim 1 wherein the transition metal salt is a zinc salt.

12. A process as claimed in claim 11 wherein the zinc salt is salt of a monobasic acid.

13. A process as claimed in claim 12 wherein the zinc salt is selected from the group consisting of zinc chloride, zinc bromide, zinc nitrate and zinc tetrafluoroborate.

14. A process as claimed in claim 1 wherein the transition metal salt is selected from the group consisting of zinc, manganese, cobalt, nickel and copper.

15. A process as claimed in claim 14 wherein the salt is a salt of a monobasic acid.

16. A process as claimed in claim 15 wherein the salt is selected from the group consisting of a chloride, bromide, nitrate, and tetrafluoroborate.

* * * * *